(12) United States Patent
Copland et al.

(10) Patent No.: US 7,544,409 B2
(45) Date of Patent: Jun. 9, 2009

(54) METHOD AND ARTICLE FOR APPLYING AND MONITORING A SURFACTANT

(75) Inventors: Donald S Copland, Brookville, IN (US); Mike E Crowley, Key West, FL (US); Jonathan B. Hall, Cincinnati, OH (US)

(73) Assignee: SpencerHall, Inc., Cincinnati, OH (US)

( * ) Notice: Subject to any disclaimer, the term of this patent is extended or adjusted under 35 U.S.C. 154(b) by 369 days.

(21) Appl. No.: 10/528,964

(22) PCT Filed: Sep. 19, 2003

(86) PCT No.: PCT/US03/29630

§ 371 (c)(1),
(2), (4) Date: Mar. 18, 2005

(87) PCT Pub. No.: WO2004/026999

PCT Pub. Date: Apr. 1, 2004

(65) Prior Publication Data

US 2006/0016352 A1 Jan. 26, 2006

(51) Int. Cl.
*B41M 5/00* (2006.01)
*B44C 1/17* (2006.01)
*G03G 7/00* (2006.01)

(52) U.S. Cl. .............. 428/195.1; 428/204; 428/205; 428/914; 424/63; 424/414; 510/130; 510/142; 510/143; 510/146; 510/438; 510/441; 510/445

(58) Field of Classification Search .............. 428/195.1, 428/204, 205, 914; 424/63, 414; 510/130, 510/142, 143, 146, 438, 441, 445
See application file for complete search history.

(56) References Cited

U.S. PATENT DOCUMENTS

| | | | | |
|---|---|---|---|---|
| 5,928,797 A | * | 7/1999 | Vineberg | 401/132 |
| 6,106,852 A | * | 8/2000 | Vineberg | 424/402 |
| 2002/0022008 A1 | * | 2/2002 | Forest et al. | 424/59 |
| 2002/0041851 A1 | * | 4/2002 | Kamimoto | 424/9.8 |
| 2002/0114764 A1 | * | 8/2002 | Berryman et al. | 424/9.1 |
| 2002/0187181 A1 | * | 12/2002 | Godbey et al. | 424/443 |
| 2003/0044366 A1 | * | 3/2003 | Dole et al. | 424/63 |

* cited by examiner

*Primary Examiner*—Callie E Shosho
*Assistant Examiner*—David J Joy
(74) *Attorney, Agent, or Firm*—Mark F. Smith; Smith Brandenburg Ltd

(57) ABSTRACT

The present invention is directed to a method and an article for performing the method of monitoring a surfactant. A preferred embodiment of the invention, an article comprises a substrate having an image and a surfactant thereon. The substrate is formed from various known fabrics or materials capable of absorbing and retaining a substantial quantity of the surfactant. During use, as the surfactant is dissipated, the image changes in appearance thereby indicating the quantity of surfactant remaining on the substrate. In a preferred embodiment of the invention, the method and article of the present invention is effective for encouraging and making washing enjoyable for children and includes the use of an epidermal surfactant, such as soap, detergent, or other active ingredient.

20 Claims, 7 Drawing Sheets

METHOD AND ARTICLE FOR APPLYING AND MONITORING A SURFACTANT

TECHNICAL FIELD

The present invention is directed to a method and an article for performing the method of applying and monitoring a surfactant and, more particularly, to a method and an article for performing the method of applying and monitoring an epidermal surfactant after it has been applied to the skin of a person.

BACKGROUND OF THE INVENTION

Various types of epidermal surfactants have been developed for applying to the skin of an individual. Surfactants, such as lathering surfactants, have been used with various types of disposable and nondisposible wash pads or washcloths for body cleansing. Unfortunately, conventional nondisposable wash pads and washcloths are difficult for children to use, who typically attempt to bunch them into a ball when washing. Occasionally, part of the cloth will flop and splash soap in the child's eye. Further, a child will often complete an entire bath using a conventional wash pad or washcloth without ever touching the soap to the pad or cloth. Additionally, a child attempting to use a wash pad or a washcloth with a conventional bar of soap will result in the child only partially soaped, with the soap often resting on the bottom of the bath tub or shower.

In order to make washing more enjoyable, soaps have been developed shaped like characters or have characters embedded within. Such soaps appeal to children and encourage them to bathe longer. Other soaps, such as decorative soaps, appeal to adults and may comprise a transparent soap having an embedded article or an embedded image layer therein. The image layer can be dissolvable or not dissolvable in water. Such decorative soaps can also encourage children to bathe longer and can be used by adults for decoration purposes. Unfortunately, while such soaps may encourage children to bathe longer, they are not always convenient and continue to be difficult for use by children.

Disposable wash pads or washcloths, such as single use, premoistened and prepackaged towelettes or wipes have been developed for use in washing. While such articles are more convenient than conventional nondisposable washcloths and can be used for a variety of applications, they do not generally appeal to children and it is often difficult to determine if the child has properly and fully washed themselves and if a quantity of soap, detergent, or other active ingredient contained within the towelette or wipe remains.

Accordingly, a need exists for a method and an article for performing the method of applying and monitoring if an amount of epidermal surfactant or other active ingredient remains to be dissolved during the application process. A need also exists for a method and an article for performing the method that encourage and make washing enjoyable for children, help ensure that children properly and fully wash themselves, and are easy and convenient, and inexpensive to manufacture.

DISCLOSURE OF THE INVENTION

The present invention is directed to a method and an article for performing the method of applying and monitoring an epidermal surfactant. More particularly, in a preferred embodiment of the invention, the method comprises the steps of placing an image to the surface of a substrate and depositing a surfactant on a defined area along the surface of the substrate, wherein the image operates to indicate the quantity or the continuing effectiveness of the surfactant. The method thereby encourages and makes washing enjoyable for children and is easy and convenient to perform. The method will further provide an indication as to when the total effective amount of surfactant has been dissolved.

In another preferred embodiment of the invention, the method of the present invention is directed for aiding children to properly and fully wash themselves.

In another preferred embodiment of the invention, the method of the present invention comprises the steps of printing an image on the surface of a substrate, depositing a surfactant onto the substrate to form an article for applying a surfactant to the skin of the user and for monitoring the condition of the surfactant.

In another preferred embodiment of the invention, the method further comprises the step of placing an image along the surface of a substrate using a printing process selected from the group consisting of offset printing, lithographic printing, flexographic printing, gravure printing, screen printing, ink jet printing, laser printing, pad printing, and digital printing processes.

In another preferred embodiment of the invention, the method further comprises the step of applying the surfactant to the surface of a substrate by the method selected from the group consisting of spraying, splashing, dipping, extrusion or coating processes.

In another preferred embodiment of the invention, the method of the present invention comprises the step of using the image as an indicator for determining when the total effective amount of surfactant has been dissolved.

In another preferred embodiment of the invention, the method of the present invention comprises the steps of placing an article for applying and monitoring a surfactant onto various parts of the user's skin, and applying a rubbing force such that the surfactant is distributed along the skin of the user.

Another preferred embodiment of the invention is an article comprising a substrate, an image positioned along the surface of the substrate, and a surfactant deposited on defined areas of the substrate.

Another preferred embodiment of the invention is an article comprising a substrate, an image positioned along the surface of the substrate, and a surfactant deposited over the surface of the image.

In another preferred embodiment of the invention, the surfactant is an epidermal surfactant.

In another preferred embodiment of the invention, the surfactant is selected from the group consisting of lathering agents, fragrance additives, vitamin compounds, skin treatment agents, anti-inflammatory activates, topical anesthetics, anti-microbial activates, anti-fungal activates, anti-viral agents, enzymes, skin exfoliating agents, anti-acne activates, anti-wrinkle, anti-skin atrophy and skin repair activates, skin barrier repair activates, non-steroidal cosmetic soothing activates, artificial tanning agents and accelerators, skin tightening activates, sunscreen activates, sebum stimulators, sebum inhibitors, anti-oxidants, protease inhibitors, anti-itch ingredients, hair growth inhibitors, 5-alpha reductase inhibitors, desquamating enzyme enhancers, anti-glycation agents, and mixtures thereof.

In another preferred embodiment of the invention, the image is formed from an ink selected from the group consisting of thermochromic inks, photochromic inks, hydrochromic inks, edible inks, and piezochromic inks.

In another preferred embodiment of the invention, the image is formed from a vegetable oil based printing ink.

In another preferred embodiment of the invention, the ink is covered with a coating effective for controlling the disappearance time of the ink.

In another preferred embodiment of the invention, the coating effective for controlling the disappearance time of the ink is formed of a wax.

In another preferred embodiment of the invention, the image is formed from a decal or a coating formed from a material that dissolves in water.

In another preferred embodiment of the invention, the decal or coating is formed from a material selected from the group consisting of hydrogels, compressed sugars, compressed salts, polymers and oligomers, gelatin, pectin, corn starch, and soaps.

In another preferred embodiment of the invention, the article comprises a substrate having a quantity of a lathering surfactant thereon and an image effective for encouraging and making washing enjoyable for children and for providing an indicator that can be used to monitor the amount of lathering surfactant that is remaining to be dissolved during the washing process.

In another preferred embodiment of the invention, the substrate is formed from a material capable of absorbing and retaining a substantial quantity of the surfactant.

In another preferred embodiment of the invention, the substrate is formed from a material selected from the group consisting of paper, cloth of natural or synthetic fiber, a sponge-like synthetic composition, and woven and non-woven materials.

In another preferred embodiment of the invention, the substrate is formed from a material selected from the group consisting of hydrogels, compressed sugars, compressed salts, polymers and oligomers, gelatin, pectin, corn starch, and soaps.

In another preferred embodiment of the invention, the article includes means for securing to the skin of the user.

In another preferred embodiment of the invention, the image operates by disappearing as the surfactant dissipates.

In another preferred embodiment of the invention, the image is a transparent image that becomes visible as the surfactant dissipates.

In another preferred embodiment of the invention, the image changes color as the surfactant dissipates.

In another preferred embodiment of the invention, the substrate has a first surface having a first surfactant thereon and a second surface having a second surfactant thereon.

Other objects and advantages of the invention will be apparent from the following description, the accompanying, drawings, and the appended claims.

BRIEF DESCRIPTION OF THE DRAWINGS

To provide a more complete understanding of the present invention and further features and advantages thereof, reference is now made to the following description taken in conjunction with the accompanying drawings, in which.

DETAILED DESCRIPTION OF THE PREFERRED EMBODIMENT

Figure 1:
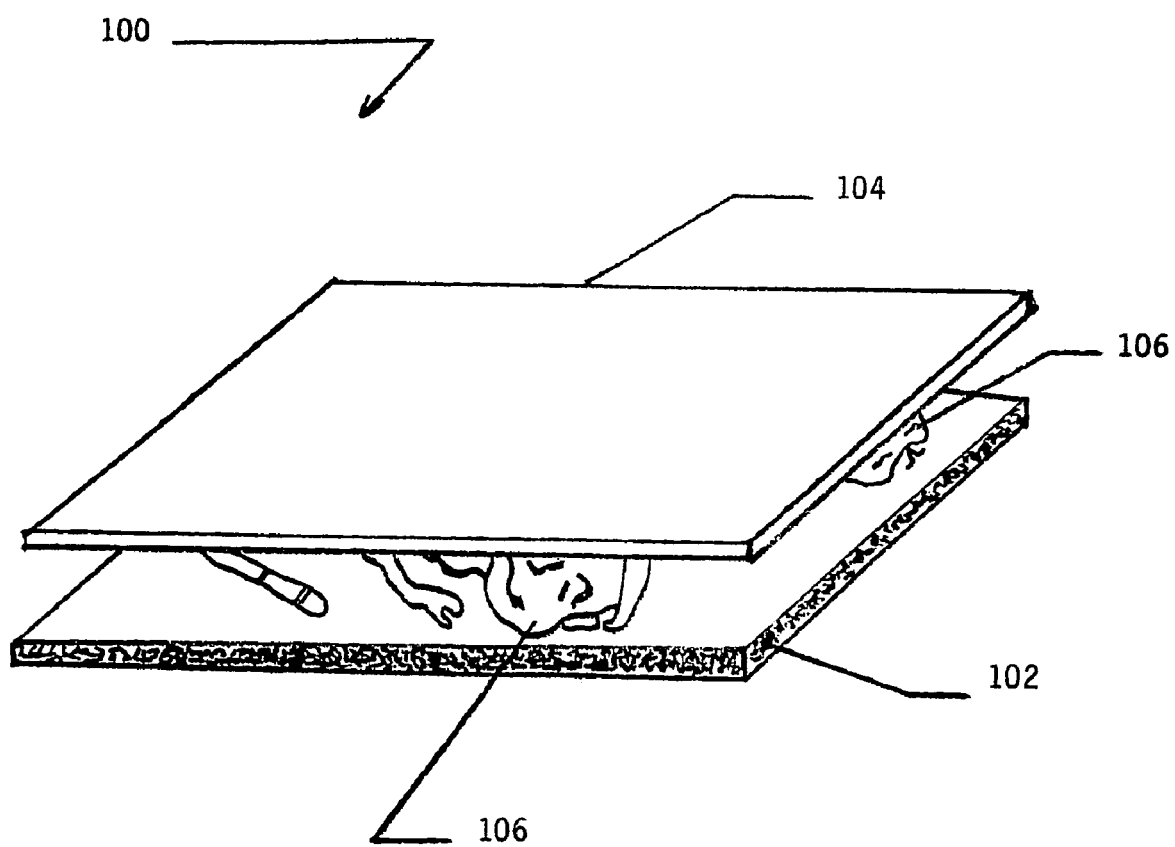
FIG. 1 is a perspective view of an article of the present invention illustrating a substrate having a surfactant deposited thereon and an image imprinted thereon.

The present invention relates to a method and an article for performing the method of monitoring a surfactant. In describing the preferred embodiments of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose.

Figure 2:
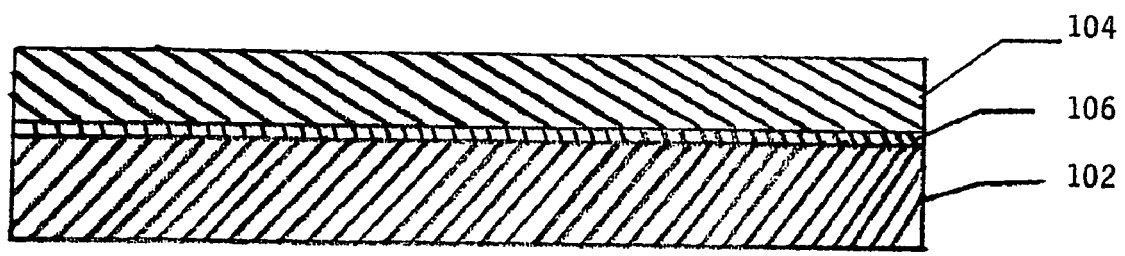
FIG. 2 is a side view of the article of FIG. 1.

The present invention is directed to a method and an article for performing the method of monitoring a surfactant. Referring to FIGS. 1 and 2, a preferred embodiment of the invention, an article 100 is shown comprising a substrate 102 effective for providing a surface for a surfactant 104. As shown, the substrate 102 is formed from various known fabrics or materials capable of absorbing and retaining a substantial quantity of the surfactant 104. Such fabrics or materials include, but not limited to, paper, cloth of natural or synthetic fiber, a sponge-like synthetic composition, such as polyurethane foam, or other woven or non-woven materials. In a preferred embodiment of the invention, the method and article of the present invention is effective for encouraging and making washing enjoyable for children and includes the use of an epidermal surfactant, such as soap, detergent, or other active ingredient. For use in washing, the composition of the substrate 102 should also be such that it resists disintegration in use for a time to effect suitable washing before the substrate 102 is discarded. Such substrates may be formed from several commercially available materials such as typically used for baby bibs, towelettes, towels and impregnated wipers. Preferably, the substrate 102 is also biodegradable upon exposure to air.

It should be understood that the article 100 of the present invention may be of any convenient size and thickness suitable for its particular purpose. For example, for use by children as an article for washing, the substrate 102 may be of about 16 square inches to about 36 square inches. For adults, it may be convenient for the size of the substrate 102 to be significantly larger, such as from 36 square inches to about 144 square inches. For use in applying lotions, perfumes, and the like, the substrate 102 may be about 4 square inches to about 36 square inches. The thickness of the substrate 102 should also be sufficient to absorb and retain adequate surfactant 104 for its intended use. This will depend on the particular composition of the substrate 102, the particular surfactant 104, and its intended use. For example, a substrate 102 formed of 100 percent cotton fiber will be able to absorb a greater volume of surfactant 104 than a substrate 102 formed of a cotton blend, such as 75 percent cotton and 25 percent of a synthethic fiber. Preferably, for most applications, the thickness of the substrate 102 is about 0.01 inch to about 0.1 inch. It should now be understood by those skilled in the art, however, that the particular size and thickness of the substrate 102 can vary greatly depending on the particular use.

Figure 3:
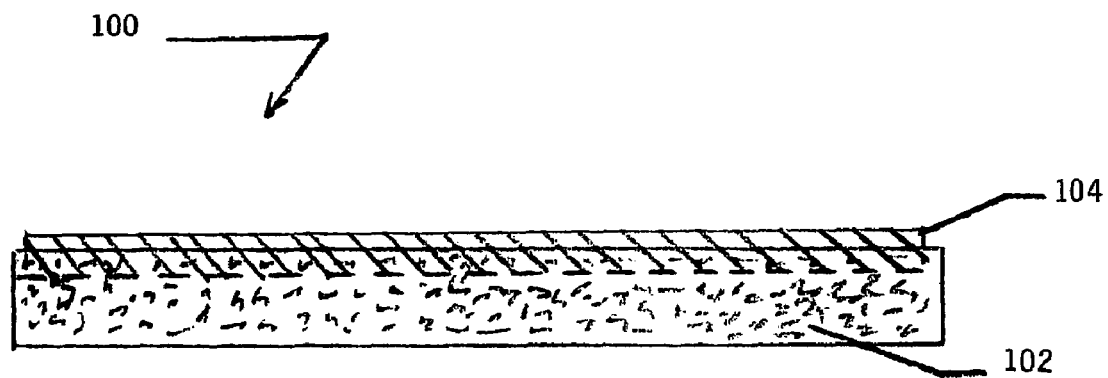
FIG. 3 is a side view of the substrate comprising the article of FIG. 1.

In a preferred embodiment of the invention, as shown in FIGS. 1 and 3, the substrate 102 is formed from a non-woven sheet of rayon and polyester fibers blended together by mechanical entanglement, and a selected portion or portions of the substrate 102 is impregnated with a desired amount of surfactant 104 such as by spraying, laser printing, splashing, dipping or coating. Preferably, the surfactant 104 is spread over the entire surface of the substrate 102 where it penetrates into the spaces between the fibers. During use, when the substrate 102 is wetted by a wetting fluid, such as water, the surfactant 104 that has penetrated into the spaces between the fibers will be released at a sufficiently slow rate so that sufficient distribution of the surfactant 104 along the skin of the user can occur.

For use in washing, the surfactant 104 can be selected from various lathering surfactants selected from the group consisting of anionic lathering surfactants, nonionic lathering surfactants, amphoteric lathering surfactants, or mixtures thereof. It should be understood that the substrate 102 may also be impregnated by other epidermal surfactants or other optional ingredients. Such surfactants and optional ingredients may include, but are not limited to, fragrance additives, vitamin compounds, skin treatment agents, anti-inflammatory activates, topical anesthetics, anti-microbial activates, anti-fungal activates, anti-viral agents, enzymes, skin exfoliating agents, anti-acne activates, anti-wrinkle activates, anti-skin atrophy and, skin repair activates, skin barrier repair activates, non-steroidal cosmetic soothing activates, artificial tanning agents and accelerators, skin tightening activates, sunscreen activates, sebum stimulators, sebum inhibitors, anti-oxidants, protease inhibitors, anti-itch ingredients, hair growth inhibitors, 5-alpha reductase inhibitors, desquamating enzyme enhancers, anti-glycation agents, and mixtures thereof.

It should be understood that in another preferred embodiment of the invention, the substrate 102 may be impregnated with one or more of the above identified epidermal surfactants and optional ingredients in combination with or without a lathering surfactant. For example, the substrate 102 may be impregnated with only sunscreen activates when the article 100 is being used to apply only a sunscreen onto the skin of the user.

In a preferred embodiment of the invention, the surfactant 104 comprises a conventional lathering surfactant that generates a colored lather often used for children's play soap.

Figure 4:
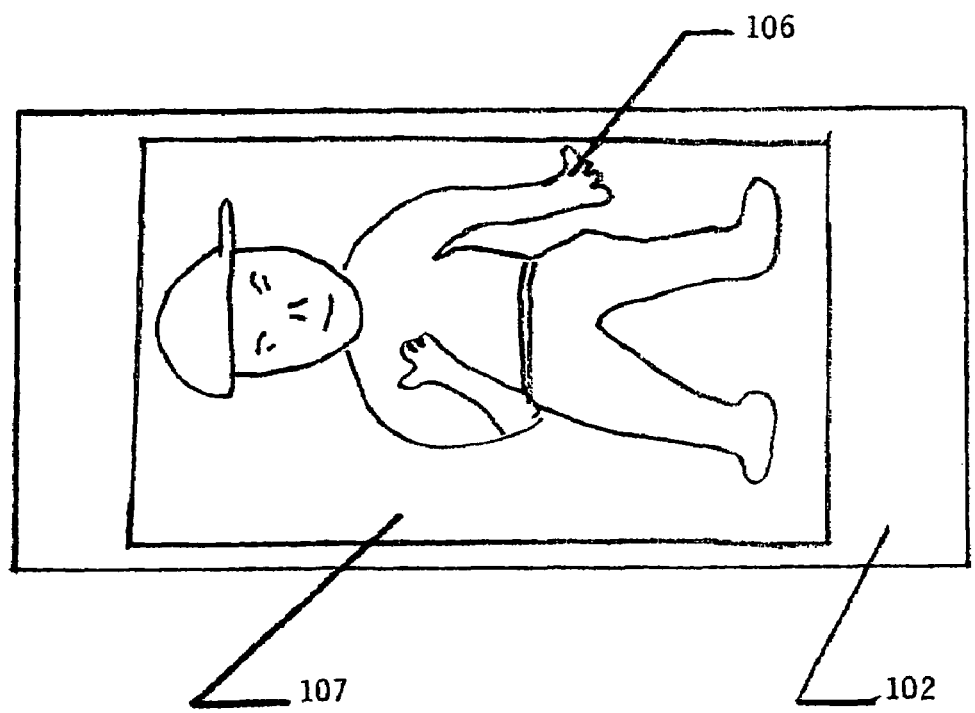
FIG. 4 is a top view of another preferred embodiment of the invention showing the substrate having an image formed from a decal or coating.
Figure 5:
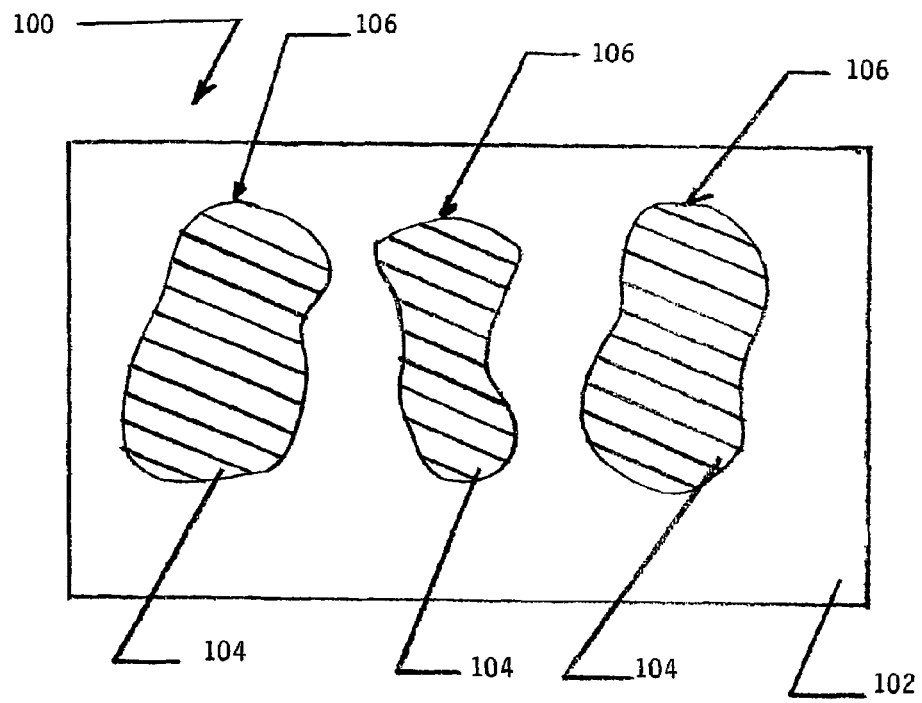
FIG. 5 is a top view of the substrate illustrating another preferred embodiment of the invention, wherein the surfactant is deposited on selected areas of the substrate.

The substrate 102 is further provided with an image 106 which is applied to the surface of the substrate 102 and may be formed from a dissolvable pigment, a decal or coating 107 (FIG. 4) effective for indicating the quantity or effectiveness of the surfactant 102. It should be understood that the image 106 and surfactant 104 may be placed at a single location along the substrate 102 and may cover the entire surface of the substrate 102 or may be placed at a plurality of selected locations thereof (FIG. 5). Such pigments may include various vegetable oil based printing inks that are hypo allergic and that can be used to form the image 106 along the surface of the substrate 102. Other inks, such thermochromic inks that change color in response to temperature fluctuations, photochromic inks that respond to variations in exposure to UV light, hydrochromics inks that change color in response to exposure to water, piezochromic inks that change color in response to pressure, and various microencapsulated inks that change color or become visible by applying an appropriate reagent may also be used. Edible printing inks that preferably produced by FDA approved ingredients that are classified as "generally recognized as safe", such as for example those sold by Sugarcraft of Hamilton Ohio (Item No. KJKCSET/PF21S) may also be used. Such inks should be relatively colorfast and have brilliant colors as well as exhibiting good transfer and adherence qualities.

Figure 6:
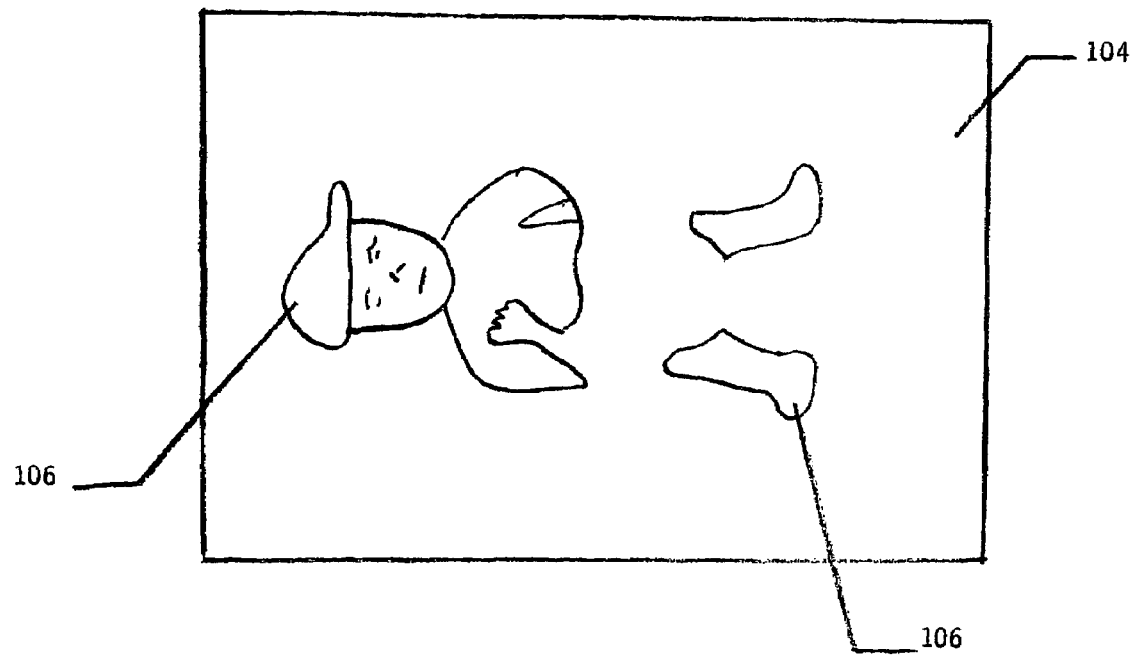
FIG. 6 of the apparatus of the present invention illustrating an example of the image showing that a portion of the surfactant has dissipated.

It should now be apparent to those skilled in the art that the specific ink for forming the image 106 along the surface of the substrate 102 is dependent on the particular use of the article 100. For example, when the article 100 is used for washing, the image may be formed using a piezochromic ink that is colorless when applied but becomes visible when rubbed or formed from a hydrochromic ink that changes color, such as from black to red, when exposed to water. During washing, as the user applies water to the article 100 and begins to rub the surface of the surfactant 104. Referring to FIG. 6, as the surfactant 104 dissolves, the image 106 becomes exposed to the water or is rubbed such that the ink forming the image 106 reacts and changes appearance (changes color or becomes visible or transparent depending on the particular ink forming the image 106). It should now be understood by those skilled in the art that as the surfactant 104 dissipates more and more of the image 106 will be exposed to the water or will be acted upon by the rubbing. Accordingly, the change in the appearance of the image 106 can be used to indicate the quantity or effectiveness of the remaining surfactant 104. Once the image 106 has completely changed, the user knows that the surfactant 104 has been dispersed.

As previously stated, decals or coatings may also be used to form the image 106 and be formed from a variety of materials that dissolve in water, such as hydrogels, compressed sugars, compressed salts, polymers and oligomers, gelatin, pectin, corn starch, soaps, and the like. As with images formed using printing inks, an image 106 formed from such decals or coatings will change in appearance when exposed to water or rubbed thereby indicating the quantity or the effectiveness of the remaining surfactant 104. In a preferred embodiment of the invention, the ink may be covered with a coating, such as a wax, that can be used to control the disappearance time of the ink.

Figure 7:
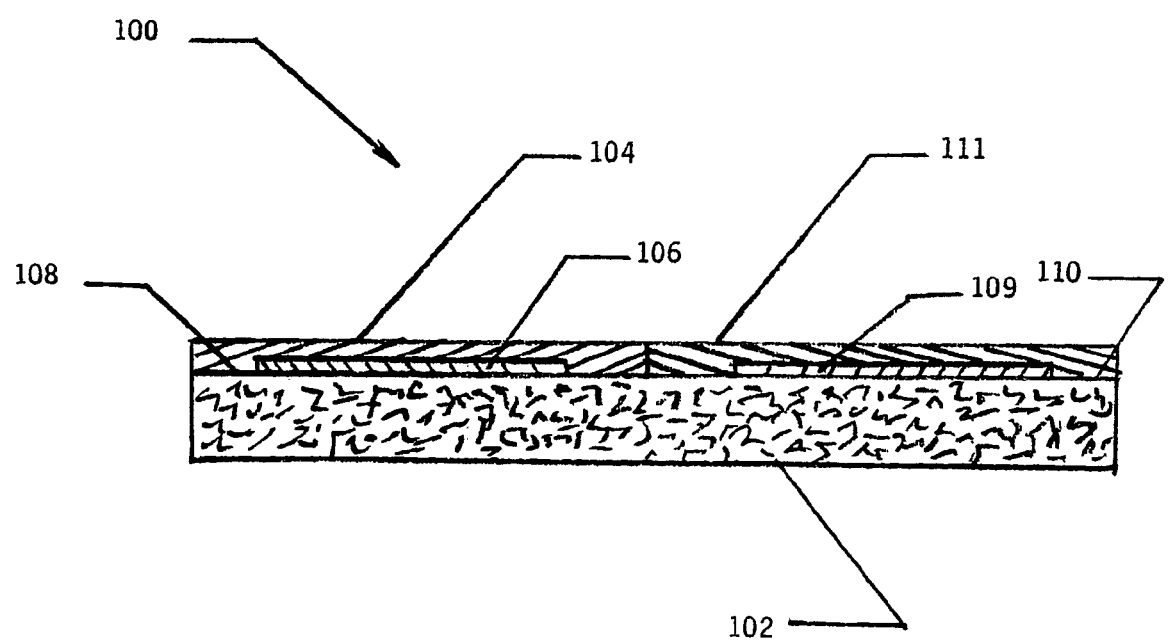
FIG. 7 is a side view of another preferred embodiment of the invention showing a substrate comprising a first surface having a first surfactant deposited thereon and a second surface having a second surfactant deposited thereon.

It should be understood to those skilled in the art that the article 100 of the present invention described hereinabove comprises a substrate 102 having a first surface 108 having an image 106 and a surfactant 104 deposited thereon, in another preferred embodiment of the invention, as shown in FIG. 7, the substrate 102 may further include a second surface 110 having a second image 109 and surfactant 111 thereon. For example, the surfactant 104 on the first surface 108 may be a lathering agent for cleansing and the surfactant 111 on the second surface 110 may be a skin moisturizer.

In order to better understand how the components above described are interrelated; the operation of the article 100 winnow be described. In a preferred embodiment of the invention, an article 100 having the desired surfactant 104, such as a lathering surfactant, is selected. The article 100 is then wetted using water that operates to produce lather and the user then bathes the body using the article 100. As the surfactant 104 dissipates, the dissolvable image 106 will begin to change in appearance (or becomes visible). The user can monitor the surfactant 104 by observing the image 106. When the image 106 has totally changes into a new appearance (or becomes totally visible), the user knows that the surfactant 104 has been totally dispensed and dissolved.

Figure 8:
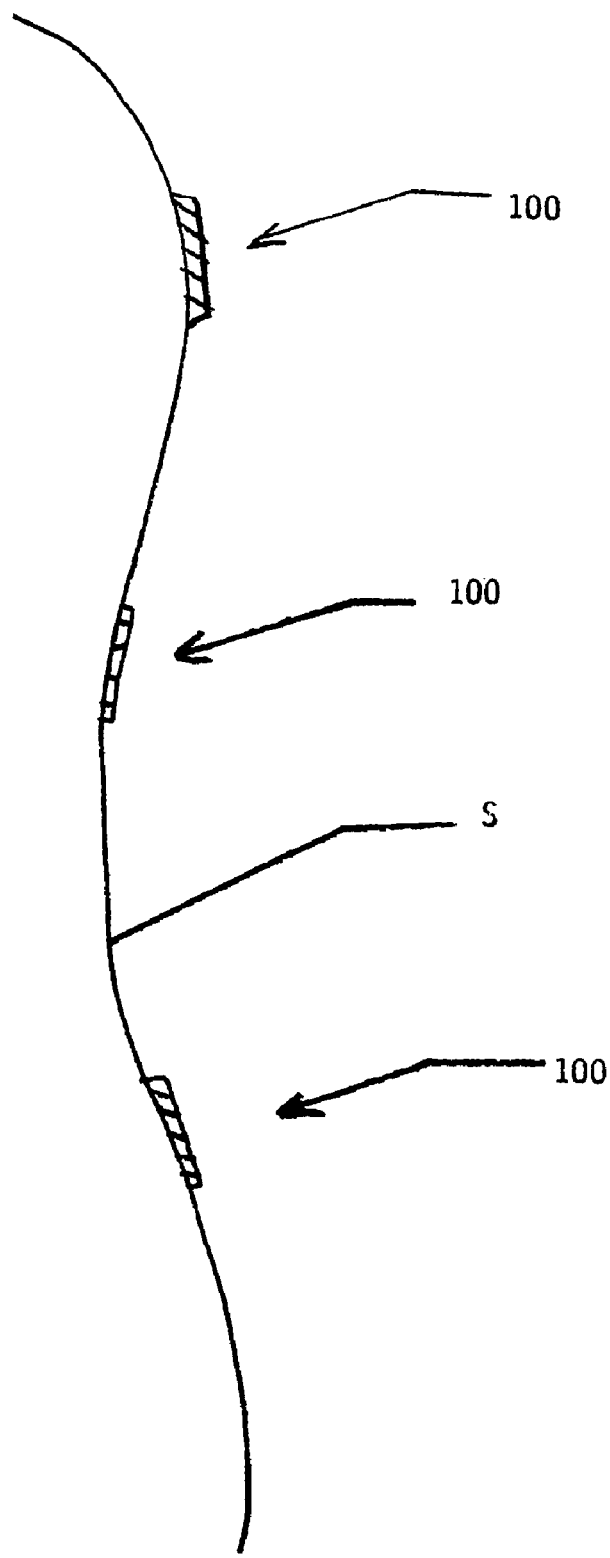
FIG. 8 is a perspective view of another preferred embodiment of the invention showing the article placed on the skin of a user.

Referring to FIGS. 1 and 8, another preferred embodiment of the invention is shown wherein the article 100 is shown attached to the skin S of the user. The substrate 102 includes an adhesive that is easily washable or is formed from a material such as hydrogels, compressed sugars, compressed salts, polymers and oligomers, gelatin, pectin, corn starch, soaps, and the like, that provide an effective amount of adhesiveness to attach the article 100 to the skin S of the user and will slowly dissolve upon exposure to water. During use, the user attaches the article 100 to parts of the body to be washed. The user then begins washing by applying a rubbing force to the article such that the surfactant 104 is distributed over the user's skin S. As washing continues, the surfactant will continue to dissipate causing the image 106 to change in appearance. As explained before, the user can then monitor the surfactant by observing the image 106. After the image 106 has completely changed, the substrate 102 will then dissolve in the wash water.

Figure 9:
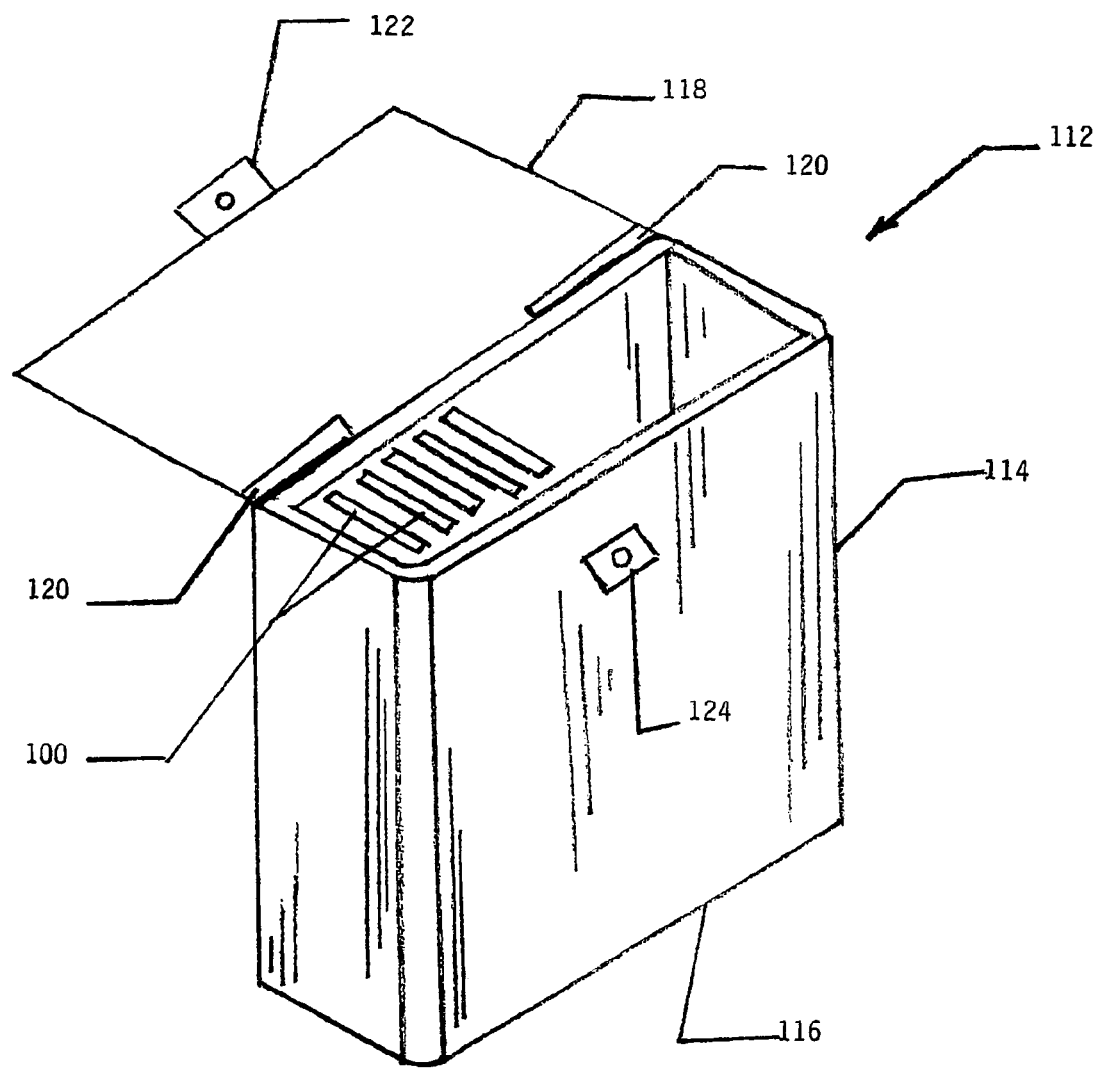
FIG. 9 is a perspective view of a container for storing a supply of cleansing articles.

Referring to FIG. 9, a typical dispenser 112 is shown that operates as a container for storing a supply of individual cleansing articles 100. It should be understood that the dispenser 112, as illustrated, may also operate as a shipping container and is designed to provide a convenient supply of cleansing articles 100. In a preferred embodiment of the invention, the dispenser 112 comprises a body 114 having a generally rectangular cross-section having a bottom 116 and a top 118. The top 118 is hinged to the body 114, such as by plastic hinges 120, for allowing the top 118 to swing into an open position permitting the user to easily remove a single article 100. The top 118 may also be provided with a flap 122 that cooperate with a detent 124 positioned on the body 114 for securing the top 118 in a closed position. It should also be understood to those skilled in the art that individual articles 100 may also be sealed in an encapsulating envelope until used. In this way an article 100 can be conveniently stored in a pocket, purse, and the like.

Although the foregoing invention has been described in some detail for purposes of clarity of understandings, it will be apparent that certain changes and modifications may be practiced within the scope of the appended claims. Furthermore, it should be noted that there are alternative ways of implementing both the method and article for implementing the method of the present invention. Accordingly, the present embodiments and examples are to be considered as illustrative and not restrictive, and the invention is not to be limited to the details given herein, but may be modified within the scope and equivalents of the appended claims.

We claim:

1. An article for applying and monitoring a surfactant, the article comprising:
   a substrate having an image applied to the surface of said substrate; and
   a surfactant placed along said surface of said substrate and covering at least a portion of said image;
   wherein said surfactant is deposited on said substrate such that said surfactant is released at a slow rate for distributing said surfactant along the skin of a user;
   wherein said image indicates the quantity or the continuing effectiveness of said surfactant.

2. The article of claim 1 wherein said surfactant is an epidermal surfactant.

3. The article of claim 1 wherein said surfactant is selected from the group consisting of lathering agents, fragrance additives, vitamin compounds, skin treatment agents, anti-inflammatory activates, topical anesthetics, anti-microbial activates, anti-fungal activates, anti-viral agents, enzymes, skin exfoliating agents, anti-acne activates, anti-wrinkle, anti-skin atrophy and skin repair activates, skin barrier repair activates, non-steroidal cosmetic soothing activates, artificial tanning agents and accelerators, skin tightening activates, sunscreen activates, sebum stimulators, sebum inhibitors, anti-oxidants, protease inhibitors, anti-itch ingredients, hair growth inhibitors, 5-alpha reductase inhibitors, desquamating enzyme enhancers, anti-glycation agents, and mixtures thereof.

4. The article of claim 1 wherein said image is ink selected from the group consisting of thermochromic inks, photochromic inks, hydrochromic inks, edible inks, and piezochromic inks.

5. The article of claim 1 wherein said image is a vegetable oil based printing ink.

6. The article of claim 1 wherein said image is a decal comprising a material that dissolves in water.

7. The article of claim 6 wherein said decal is a material selected from the group consisting of hydrogels, compressed sugars, compressed salts, polymers and oligomers, gelatin, pectin, corn starch, and soaps.

8. The article of claim 1 wherein said image is a coating comprising a material that dissolves in water.

9. The article of claim 8 wherein said coating is a material selected from the group consisting of hydrogels, compressed sugars, compressed salts, polymers and oligomers, gelatin, pectin, corn starch, and soaps.

10. The article of claim 1 wherein said substrate is a material capable of absorbing and retaining a quantity of the surfactant.

11. The article of claim 1 wherein the substrate is a material selected from the group consisting of paper, cloth or natural or synthetic fiber, a polyurethane foam, and woven and non-woven materials.

12. The article of claim 1 wherein said substrate is a material selected from the group consisting of hydrogel, compressed sugars, compressed salts, polymers and oligomers, gelatin, corn starch, and soaps.

13. The article of claim 1 further comprising means for securing to the skin of the user.

14. The article of claim 1 wherein said image operates by disappearing as the surfactant dissipates.

15. The article of claim 1 wherein said image is a transparent image that becomes visable as the surfactant dissipates.

16. The article of claim 1 wherein said image changes color as the surfactant dissipates.

17. The article of claim 1 wherein the image is covered by a coating effective for controlling the disappearance time of the image.

18. The article of claim 17 wherein said coating is formed from a wax.

19. An article for applying and monitoring a surfactant comprising:
   a substrate having an image applied to the surface of said substrate;
   wherein said substrate has a first surface having a first surfactant thereon and a second surface having a second surfactant thereon;
   wherein said image indicates the quantity or the continuing effectiveness of said first surfactant; and
   wherein said first surfactant is placed along said first surface of said substrate such that said first surfactant covers at least a portion of said image.

20. A method of applying and monitoring an epidermal surfactant applied to the skin of a person comprising the steps of:
   placing an image along the surface of a substrate; and
   placing a surfactant along the surface of said substrate such that the surfactant covers at least a portion of said image;
   wherein said surfactant is deposited on said substrate such that said surfactant is released at a slow rate for distributing said surfactant along the skin of a user;
   wherein the image indicates the quantity or the continuing effectiveness of said surfactant.

* * * * *